United States Patent [19]

Kanda et al.

[11] Patent Number: 5,254,734
[45] Date of Patent: Oct. 19, 1993

[54] METHOD FOR PREPARING AN OXIME

[75] Inventors: Yu Kanda, Kitakyushu; Takeshi Matsuoka, Kikakyushu; Haruo Habu, Kitakyushu; Tsutomu Yonemori, Mizumaki, all of Japan

[73] Assignee: Mitsubishi Kasei Corporation, Tokyo, Japan

[21] Appl. No.: 832,321

[22] Filed: Feb. 7, 1992

[30] Foreign Application Priority Data

Feb. 13, 1991 [JP] Japan .................................. 3-20130

[51] Int. Cl.$^5$ ............................................ C07C 249/08
[52] U.S. Cl. ................................................ 564/259
[58] Field of Search ....................... 564/300, 301, 259

[56] References Cited

U.S. PATENT DOCUMENTS 3,661,996  9/1992  Bader et al. ......................... 564/301

FOREIGN PATENT DOCUMENTS 0154653  6/1988  Japan .

Primary Examiner—Allen J. Robinson
Assistant Examiner—Peter G. O'Sullivan
Attorney, Agent, or Firm—Oblon, Spivak, McClelland, Maier & Neustadt

[57] ABSTRACT

A method for preparing an oxime, which comprises partitioning an aqueous hydroxylamine salt solution phase and a ketone or aldehyde phase by a cation exchange membrane, and permitting hydroxylamine in the aqueous hydroxylamine salt solution phase to diffuse and transfer through the membrane to the ketone or aldehyde phase and to form an oxime in the ketone or aldehyde phase.

8 Claims, 1 Drawing Sheet

METHOD FOR PREPARING AN OXIME

BACKGROUND OF THE INVENTION

1. Field of the Invention

The present invention relates to a method for preparing an oxime. More particularly, it relates to a novel method for producing an oxime whereby an oxime can be produced from a corresponding ketone or aldehyde and a hydroxylamine without producing a by-product of an inorganic salt such as ammonium sulfate.

2. Discussion of Background

For example, cyclohexanone oxime is industrially useful as an intermediate for producing caprolactam as a starting material for nylon. It is usually prepared by reacting cyclohexanone synthesized by various methods, with hydroxylamine.

However, in such a method, it is necessary to use hydroxylamine in the form of an inorganic salt such as a sulfate or hydrochloride for the stability of hydroxylamine, and it is necessary to neutralize such a salt with an alkali such as ammonia in the reaction system. Consequently, a substantial amount of an inorganic salt such as ammonium sulfate is produced inevitably as by-product together with the desired cyclohexanone oxime. Therefore, it has been desired to develop a process for producing a cyclohexanone oxime without producing an inorganic salt such as ammonium sulfate, as by-product. Some proposals have been made, but none of them has been fully satisfactory.

SUMMARY OF THE INVENTION

Under these circumstances, the present inventors have conducted an extensive research with an aim to control the formation of ammonium sulfate in the reaction for forming an oxime from a hydroxylamine salt and a ketone or an aldehyde and as a result, have found that by partitioning an aqueous hydroxylamine salt solution and a ketone or an aldehyde by a cation exchange membrane, hydroxylamine diffuses and transfers by ion exchange as ammonium ions to the ketone or aldehyde phase, whereupon an oxime is formed in the ketone or aldehyde phase. The present invention has been accomplished on the basis of this discovery.

Thus, the present invention provides a method for preparing an oxime, which comprises partitioning an aqueous hydroxylamine salt solution phase and a ketone or aldehyde phase by a cation exchange membrane, and permitting hydroxylamine in the aqueous hydroxylamine salt solution phase to diffuse and transfer through the membrane to the ketone or aldehyde phase and to form an oxime in the ketone or aldehyde phase.

DETAILED DESCRIPTION OF THE PREFERRED EMBODIMENTS

Figure 1:
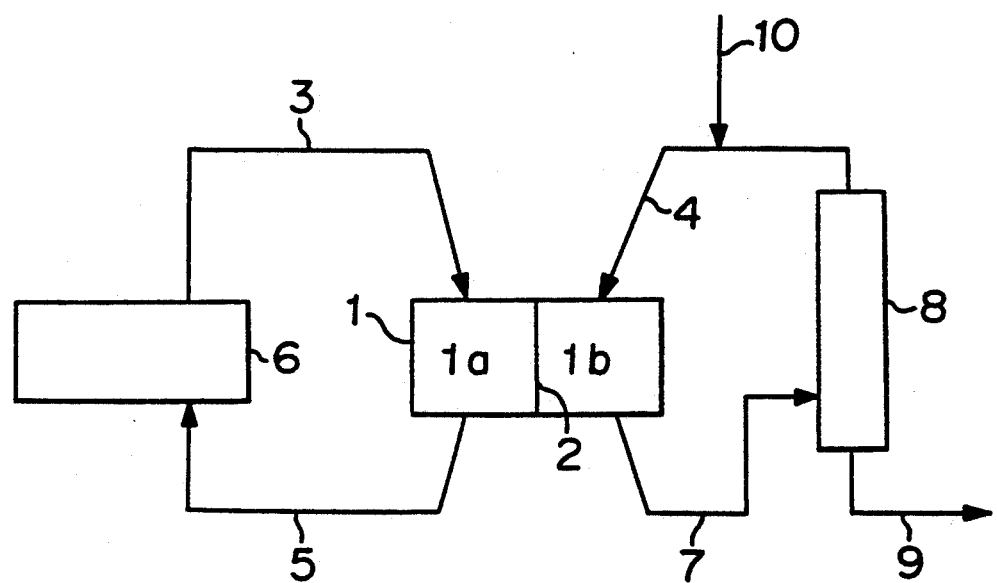
FIG. 1 is a diagrammatical view illustrating the process for producing an oxime according to the present invention, in which reference numeral 1 indicates a reactor, numeral 1a indicates an aqueous phase side of the reactor, numeral 1b indicates an oil phase side of the reactor, numeral 2 indicates an ion exchange membrane, numerals 3, 4, 5, 7, 9 and 10 indicate conduits, numeral 6 indicates a hydroxylamine salt synthesis system, and numeral 8 indicates an oxime separation system.

Now, the present invention will be described in detail.

The hydroxylamine salt to be used in the present invention may be a sulfate, a hydrochloride, a phosphate or a formate. Usually, a sulfate is commonly employed. The concentration of the hydroxylamine salt in the aqueous solution is usually from 5 to 60% by weight, preferably from 10 to 50% by weight. If the concentration is lower than this range, an efficient reaction can not be expected. On the other hand, if the concentration is higher than this range, hydroxylamine tends to precipitate, such being undesirable.

On the other hand, the ketone to be used in the present invention, may be an aliphatic, alicyclic or aromatic compound, such as cyclohexanone, cyclododecanone, acetone, dimethylacetone, acetophenone or benzophenone. The aldehyde may be, for example, acetaldehyde, propionaldehyde, butylaldehyde, caproic aldehyde, benzaldehyde or anisaldehyde. From the industrial viewpoint, cyclohexanone which can be a starting material of caprolactam, is particularly preferred among these ketones and aldehydes. The amount of the ketone or aldehyde phase is usually from 0.1 to 10 times by volume, preferably from 0.5 to 5 times by volume, to the aqueous hydroxylamine salt solution phase, although it varies depending upon the reaction system.

The cation exchange membrane to be used in the present invention is the one having cation exchange groups introduced to a synthetic resin membrane as the base material and is known as an ion exchange membrane. As the cation exchange groups, those having strong acid type ion exchange groups, particularly sulfonic acid groups, are commonly employed. In the present invention, they are used in a free acid form. The ion exchange capacity of the cation exchange membrane is not particularly limited, but is usually within a range of from 0.1 to 10 meq/g·dry resin, preferably from 0.5 to 3 meq/g·dry resin. The base resin constituting the cation exchange membrane may, usually, be an acrylonitrile-vinyl chloride copolymer, a styrene-divinylbenzene copolymer, or a modified ethylene-tetrafluoride polymer. Further, the thickness of the cation exchange membrane is usually from 0.05 to 3 mm, preferably from 0.2 to 2 mm. A commercially available membrane may be used as it is, as such a cation exchange membrane.

The reaction temperature is usually from 10° to 100° C., preferably from 20° to 80° C. The reaction time is properly selected usually within a wide range of from 0.5 to a few hundred hours depending upon the area and the ion exchange capacity of the cation exchange membrane. Further, the reaction pressure may be at atmospheric pressure. However, if necessary, the aqueous hydroxylamine salt solution phase may be maintained under a pressurized system.

For the reaction in the present invention, the aqueous hydroxylamine salt solution phase and the ketone or aldehyde phase are partitioned by a cation exchange membrane, whereby hydroxylamine selectively diffuses and transfers from the aqueous hydroxylamine salt solution phase to the ketone or aldehyde phase through the cation exchange membrane as ammonium ions and reacts in the ketone or aldehyde phase to form the corresponding oxime, while and an acid is freed in the aqueous hydroxylamine salt solution phase.

As the basic reaction system, a reactor is employed which has two compartments partitioned by the ion exchange membrane, and an aqueous hydroxylamine salt solution is charged into one compartment, and a liquid of a ketone or an aldehyde is charged to the other compartment, whereupon the respective phases are circulated and withdrawn in a batch system or in a continuous system. Otherwise, it is possible to employ a flow operation system using a reactor having a plurality of compartments partitioned by ion exchange membranes reinforced by mesh-form supporting materials.

After completion of the reaction, the oxime can readily be separated and recovered from the mixture containing the oxime in the ketone or aldehyde phase side, by distillation, crystallization or extraction. Further, the ketone or aldehyde after the separation, can be recycled to the reaction system. In a case where a small amount of an acid has entered to the ketone or aldehyde phase, the acid may be treated by e.g. neutralization, before recovery of the oxime.

On the other hand, the acid freed in the aqueous hydroxylamine salt solution phase is preferably recovered and reused without neutralization. Namely, without isolating the acid, the aqueous hydroxylamine salt solution having the concentration of the free acid such as sulfuric acid increased, is recovered, and the recovered solution may be used as a solvent by itself or with a further addition of concentrated sulfuric acid, if necessary, for the reaction of nitrogen monoxide with hydrogen to produce a hydroxylamine salt as the starting material.

To conduct the method for preparing the oxime of the present invention on an industrial scale, a process as shown in FIG. 1, may, for example, be employed.

Referring to FIG. 1, a reactor 1 is divided into two compartments by an ion exchange membrane 2. To one supplied from a conduit 3, and to the other compartment 1b, a ketone or aldehyde is supplied from a conduit 4. In the aqueous hydroxylamine salt solution phase side (aqueous phase side) 1a, a free acid is formed, and a part of the aqueous solution containing the free acid and an unreacted hydroxylamine salt, is returned via a conduit 5 to a hydroxylamine salt synthesis system 6. For the synthesis of a hydroxylamine salt, a method may be mentioned wherein nitrogen monoxide is catalytically reduced with hydrogen in a dilute aqueous solution of a mineral acid such as sulfuric acid in the presence of a platinum-supported catalyst in a suspended state. This reaction is conducted usually at a temperature of from 40° to 80° C. under atmospheric pressure or elevated pressure. The hydroxylamine salt produced in this synthesis system, can be supplied via a conduit 3 to the aqueous phase side 1a of the reactor.

On the other hand, in the ketone or aldehyde phase side (oil phase side) 1b, an oxime is formed, and a part of a mixture comprising the oxime and an unreacted ketone or aldehyde, is withdrawn from a conduit 7, whereupon the oxime is separated in a separation system 8 and recovered from a conduit 9. As a specific separating means for the separation system 8, a reduced pressure distillation method may be mentioned. Further, in order to remove a very small amount of an acid which may enter into the oil phase, it is preferred to neutralize the mixture with a small amount of alkali before conducting the distillation (not shown). After the separation of the oxime, the remaining ketone or aldehyde is recycled via a conduit 4 to the oil phase side 1b of the reactor. At that time, the ketone or aldehyde corresponding to the formed and recovered oxime, may be supplied afresh from a conduit 10.

Now, the present invention will be described in further detail with reference to Examples. However, it should be understood that the present invention is by no means restricted to such specific Examples.

EXAMPLE 1

A 200 ml glass container was partitioned along the center by a sulfonic acid type ion exchange membrane ($H^+$ type, an acrylonitrile-vinyl chloride copolymer type polymer, membrane area: 33 $cm^2$ membrane thickness: 0.6 mm, ion exchange capacity: 2.7 meq/g·dry resin). To one side, 85 ml of a 5.0N hydroxylamine sulfate aqueous solution was charged, and to the other side, 70.4 g of cyclohexanone was charged, whereupon the respective phases were left to stand for five hours under stirring at 25° C. Then, the solutions of the respective phases were analyzed by gas chromatography, whereby as shown in Table 1, it was found that 0.018 mol of cyclohexanone oxime was formed in the cyclohexanone phase (oil phase) (the molar yield of the formed oxime to the charged hydroxylamine equivalent was 4.2%). Formation of any other by-products was not observed. On the other hand, in the aqueous hydroxylamine sulfate solution phase (aqueous phase), free sulfuric acid was found in an amount substantially equivalent to the formed oxime.

EXAMPLES 2 TO 4

The operation was conducted in the same manner as in Example 1 except that the reaction temperature or the thickness of the ion exchange membrane was changed as shown in Table 1. The results are shown in Table 1. Other than cyclohexanone oxime, no formation of any by-products was observed.

TABLE 1

| Example No. | Reaction temp. (°C.) | Membrane thickness (mm) | Aqueous phase | | Oil phase | |
| --- | --- | --- | --- | --- | --- | --- |
| | | | Amount of recovered sulfuric acid (equivalent) | Amount of oxime inclusion (mol) | Amount of formed oxime (mol) | Amount of sulfuric acid inclusion (equivalent) |
| 1 | 25 | 0.6 | 0.020 | $7 \times 10^{-4}$ | 0.018 | 0.002 |
| 2 | 50 | 0.6 | 0.026 | $1 \times 10^{-3}$ | 0.025 | 0.004 |
| 3 | 75 | 0.6 | 0.044 | $5 \times 10^{-3}$ | 0.041 | 0.006 |
| 4 | 25 | 1.2 | 0.007 | $1 \times 10^{-4}$ | 0.008 | 0.001 |

According to the present invention, simply by partitioning the aqueous hydroxylamine salt solution phase and the ketone or aldehyde phase by a cation exchange membrane and maintaining the liquid phases, the desired oxime is obtained in the ketone or aldehyde phase. The reason is such that from the aqueous hydroxylamine salt solution phase, hydroxyl ammonium ions are selectively permiated through the membrane by ion exchange and diffuse to the ketone or aldehyde phase. It was totally unexpected and surprising that such a phenomenon can be brought about by a cation exchange membrane. As a result, according to the present

What is claimed is:

1. A method for preparing an oxime, which comprises partitioning an aqueous hydroxylamine salt solution phase and a ketone or aldehyde phase by a cation exchange membrane, and permitting hydroxylamine in the aqueous hydroxylamine salt solution phase to diffuse and transfer through the membrane to the ketone or aldehyde phase and to form an oxime in the ketone or aldehyde phase, wherein the concentration of the hydroxylamine salt in the aqueous solution is from 5 to 60% by weight, the volume of the ketones or aldehyde phase is from 0.1 to 10 times the volume of the aqueous hydroxylamine salt solution phase.

2. The method according to claim 1, wherein the ketone or aldehyde phase containing the formed oxime, is withdrawn from the ketone or aldehyde phase side (1b) of the reactor, and after the oxime is separated and recovered therefrom, the residual solution is recycled to the ketone or aldehyde phase side (1b) of the reactor.

3. The method according to claim 1, wherein the aqueous hydroxylamine salt solution is withdrawn from the aqueous hydroxylamine salt solution phase side (1a) of the reactor and supplied to a hydroxylamine salt synthesis system, and a reaction solution from the synthesis system is recycled to the aqueous hydroxylamine salt solution side (1a) of the reactor.

4. The method according to claim 1, wherein the ion exchange groups of the cation exchange membrane are sulfonic acid groups.

5. The method according to claim 1, wherein the cation exchange membrane has a thickness of from 0.05 to 3 mm.

6. The method according to claim 1, wherein the reaction temperature is from 10° to 100° C.

7. The method according to claim 1, wherein the ketone is cyclohexanone.

8. The method according to claim 1, wherein the hydroxylamine salt is a sulfate.

* * * * *